United States Patent [19]

Yamashita

[11] Patent Number: 5,582,627
[45] Date of Patent: Dec. 10, 1996

[54] DETOXIFICATION OF SOIL

[76] Inventor: Thomas T. Yamashita, 2030 N. Berkeley Ave., Turlock, Calif. 95380

[21] Appl. No.: 572,492

[22] Filed: Aug. 23, 1990

Related U.S. Application Data

[63] Continuation-in-part of Ser. No. 242,951, Sep. 9, 1988, abandoned, Ser. No. 354,155, May 19, 1989, abandoned, and Ser. No. 490,351, Mar. 8, 1990.

[51] Int. Cl.⁶ ..................................................... C05F 5/00
[52] U.S. Cl. ................................... 71/26; 71/11; 71/64.1
[58] Field of Search ............................ 71/903, 804, 6–8, 71/11, 23, 26

[56] References Cited

U.S. PATENT DOCUMENTS

| | | | |
|---|---|---|---|
| 2,756,134 | 7/1956 | Novak | 71/1 |
| 3,353,949 | 11/1967 | Nau | 71/64 |
| 3,640,698 | 2/1972 | Backlund | 71/29 |
| 3,753,722 | 8/1973 | Beucler | 99/2 |
| 3,846,290 | 11/1974 | Raymond | 210/11 |
| 4,033,745 | 7/1977 | Moore | 71/28 |
| 4,119,429 | 10/1978 | Louness | 71/903 X |
| 4,401,762 | 8/1983 | Tellier | 435/243 |
| 4,493,895 | 1/1985 | Colaruotolo | 435/262 |
| 4,652,294 | 3/1987 | Arnold | 71/28 |
| 4,727,031 | 2/1988 | Brown | 435/244 |
| 4,849,360 | 7/1989 | Norris | 435/264 |
| 4,925,802 | 5/1990 | Nelson | 435/262 |
| 4,952,229 | 8/1990 | Muir | 71/904 X |

FOREIGN PATENT DOCUMENTS

| | | | |
|---|---|---|---|
| 0161395 | 11/1985 | European Pat. Off. | |
| 68022206 | of 0000 | Japan . | |
| 57-055986 | 4/1982 | Japan . | |
| 0158286 | 9/1982 | Japan | 71/903 |
| 1200193 | 9/1986 | Japan | 71/903 |

Primary Examiner—Ferris Lander
Attorney, Agent, or Firm—Flehr, Hohbach, Test, Albritton & Herbert

[57] ABSTRACT

Compositions for and method of degrading organic chemicals in soil. The composition is a nutrient medium serving as a substrate for micro-organisms in the soil, preferably containing a major proportion of a source of carbon skeleton and energy, a macronutrient component preferably including nitrogen and other macronutrients, and a micronutrient component, preferably also a complexing agent and a vitamin/co-factor component. This nutrient material is added to soil, e.g. soil contaminated by a pesticide, to cause proliferation of micro-organisms which are effective, or which develop effectiveness to degrade the organic chemicals. Preferably the micro-organisms are those naturally present in the soil but useful micro-organisms may be added with the nutrient medium.

13 Claims, No Drawings

DETOXIFICATION OF SOIL

This application is a continuation-in-part of the following patent applications: Ser. No. 242,951, filed Sep. 9, 1988, entitled "COMPOSITION FOR AND METHOD OF TREATING PLANTS", now abandoned; Ser. No 354,155, filed May 19, 1989, entitled "METHOD OF APPLYING ENERGY, CARBON SKELETON AND NUTRIENT MATERIALS TO VEGETATION"; now abandoned; and Ser. No. 490,351, filed Mar. 8, 1990, entitled "METHOD AND COMPOSITION FOR PROMOTING AND CONTROLLING GROWTH OF PLANTS," which has been allowed.

FIELD OF THE INVENTION

This invention relates to the treatment of soil to improve its characteristics for growing vegetation and it relates more particularly to the treatment of soil that has been contaminated by chemicals such as herbicides and other pesticides.

BACKGROUND OF THE INVENTION

In my co-pending applications referred to above, the treatment of soil to improve its properties is described including buffering plant roots from harmful, toxic levels of chemicals and/or elements and degrading of harmful chemicals in soil.

This invention is particularly concerned with the detoxification of soil that has become contaminated by chemicals that have been applied directly to the soil, for example as a herbicide, or indirectly as by drainage of water or moisture from plants that have been treated with a chemical; also indirectly by the decay of plants that have been treated by chemicals and the mixing of the products of decay with the soil.

This invention is also concerned with the treatment of contaminated soil generally including the treatment of landfills and other soil which has become contaminated with toxic chemicals of various types which are organic in nature and it may have application to treatment of soil contaminated by metals.

The contamination of soil by chemicals applied to the soil directly or indirectly is a serious problem owing to the persistence of such chemicals in the soil which render it unfit for the raising of crops or of lesser use, and also the growth of other vegetation.

Heretofore soil contaminated by toxic chemicals has been detoxified, at least to some extent, by pH effects and hydrolysis, by photochemical effects and by chemical reactions. Residual pesticides have been degraded by unassisted microbiota, either added as such or naturally present in soil.

Such methods have been undependable and have not had consistent success.

OBJECTS OF THE INVENTION

It is an object of the invention to provide improvements in the detoxification of contaminated soil.

It is a particular object of the invention to provide a method, and a composition for practice of the method, which are superior to methods and compositions used heretofore and which have one or more of the advantages of economy, speed of results, and a wide spectrum of applications to toxicants.

The above and other objects will be apparent from the ensuing description and the appended claims.

SUMMARY OF THE INVENTION

In accordance with the present invention soil contaminated with a chemical is treated with a nutrient material which will cause proliferation of micro-organisms that degrade the chemical into non-toxic products.

This may be done after the contaminating chemical has had its intended effect, for example as a herbicide, to rid the soil of residues of the chemical; or the nutrient material may be applied to the soil before application of the toxic chemical to the soil, or at the time of application, or shortly after application of the chemical to the soil. Where the nutrient material is applied at an early stage, that is before the chemical has had its intended effect, care should be taken to avoid or to minimize interference of the nutrient material with the intended action of the chemical. Further, the effect of the nutrient material, through the medium of the micro-organisms proliferated by its presence, may act upon and further degrade an intermediate degradation product of the added chemical.

The nutrient material may be added with or without added micro-organisms. That is, the nutrient material may be added alone to proliferate microbiota already in the soil, or micro-organisms may be added to, or along with the nutrient material.

The nutrient material may be any plant nutrient capable of causing proliferation of the desired micro-organisms but it is preferably a balanced material such as that described in the examples below which include as the major component (other than water) a carbon skeleton/energy component, a macronutrient component including a source of nitrogen and a micro-nutrient component and preferably also a complexing agent such as an alginate, a lignosulfonate, etc. Preferably the nutrient material also contains a vitamin/cofactor component.

The nutrient material may be applied in various ways, for example by adding it to irrigation water or by sprinkling or spraying it onto the soil or as a dust or granular material which is mixed with the soil, also in the form of a suspension in water.

Although the invention is described primarily with respect to toxic chemicals such as pesticides, it is applicable to the degradation of organic materials generally, for example waste materials generally, examples being automobile tires that have been finely shredded and mixed with soil.

DETAILED DESCRIPTION OF THE INVENTION

It is known that micro-organisms normally present in soil are effective in degrading toxic substances in the soil. However these micro-organisms have not been used efficiently heretofore. For example what may be described as xenobiotic components, that is chemicals that are foreign to the natural soil environment, are seldom degraded by a single species or group of microbes.

In accordance with the present invention the natural microbiota in soil are stimulated and nourished to cause the proliferation of many species, some of which will effectively degrade chemicals or will acquire, by natural adaptation, the ability to do so.

For that purpose, and in the preferred practice of the invention, a balanced nutritive is added to the soil which will favor the rapid proliferation of different species and strains of microbiota. Such balanced nutritive is described in the aforesaid co-pending applications as follows:

1. Assimilable carbon skeleton/energy component.
2. Macronutrient component.
3. Micronutrient component.

In the preferred composition the following additional components are also present:

4. Vitamin/cofactor component.
5. Enhancement agent component.

A buffer is also used to adjust the pH of the composition.

Example 1 below illustrates a composition, which is useful in the practice of the invention.

EXAMPLE 1

Sugar beet molasses was used as stock material and source of energy and carbon skeleton. The total invert sugar (TSI) level was brought to 40% by dilution with water. Following are ingredients used to make the molasses blend:

| Macronutrients | | (Elemental) d% w/v | Source of Element |
|---|---|---|---|
| Nitrogen | (N) | urea (0.65) KN03 (0.60) total = 1.25% | Urea, Potassium nitrate |
| Phosphorus | (P) | 1.5 | Phosphoric acid |
| Potassium | (K) | 2.0 | Potassium nitrate |
| Calcium | (Ca) | 2.0 | Calcium gluconate |
| Magnesium | (Mg) | 0.5 | Magnesium sulfate |
| Sulfur | (S) | 3.5 | Various sulfates |
| Micronutrients | | | |
| Zinc | (Zn) | 1.0 | Zinc sulfate |
| Iron | (Fe) | 1.0 | Ferrous sulfate |
| Manganese | (Mn) | 1.0 | Manganese sulfate |
| Copper | (Cu) | 0.5 | Cupric sulfate |
| Boron | (B) | 0.02 | Boric acid |
| Molybdenum | (Mo) | 0.03 | Ammonium molybdate |
| Cobalt | (Co) | 0.03 | Cobalt nitrate |
| Vitamins and Cofactors | | | |
| Thiamine | (B1) | 0.02 | Thiamine hydrochloride |
| Riboflavin | (B2) | 0.02 | Riboflavin |
| Nicotinic acid | | 0.02 | Nicotinic acid |
| Pyridoxine | (B6) | 0.02 | Pyridoxine hydrochloride |
| Folic acid | | 0.02 | Folic acid |
| Biotin | | 0.02 | Biotin |
| Pantothenic acid | | 0.02 | Pantothenic acid (calcium salt) |
| Cyanocobalamin | | 0.02 | Vitamin B12 |
| Phosphatidylcholine | | | 0.02 Lecithin |
| Inositol | | 0.02 | Inositol |
| Para-aminobenzoic acid | | 0.02 | PABA |
| Enhancement Agents | | | |
| Seaweed extract | | 2.5% (v/v) | Seaweed extract (cold processed) |
| Citric acid | | 10.0 gr/gal mix | Citric acid |
| Katy-J Complexing Agent | | 0.5 gr/gal mix | Katy-J (JKT Corp.) |
| Xanthan gum | | 0.07 (v/v) | Xanthan gum |
| Sugars and Carbon Skeletons | | | |
| Molasses | | 40% (TSI) | Beet molasses |
| Buffers | | | |
| Phosphate buffer (pH = 6) | | 0.02% | Phosphate buffer |

The most important macronutrients are nitrogen, phosphorus, potassium and calcium but it is preferred that the others also be present. The more important micronutrients are zinc, iron and manganese but it is preferred that the others also be present.

The term "Enhancement Agents" used above is intended to include complexing agents, gums and growth regulators. See the discussion below under the caption "Discussion of Components."

Mixing Instructions

While under rapid mechanical or hydraulic agitation, water and two thirds of the total molasses volume are mixed. The amount of added water should represent approximately 15% of the molasses volume. Ingredients are then slowly metered into the batch in the following order:

1. Citric acid
2. Katy-J Complexing Agent
3. Phosphoric acid
4. Nitrogen
5. Potassium
6. Micronutrients (separately)
7. Vitamins and cofactors
8. Seaweed extract
9. Xanthan gum Water is again added to the mix to establish a total invert sugar (TSI) concentration of ≈40%. As the TSI of molasses may vary, necessary water volumes may vary accordingly.

As the parent molasses may contain potassium concentrations as much as 2.0–7.0%, it may be necessary to omit potassium nitrate. If potassium nitrate is omitted, the nitrogen may be supplied in total by urea (1.25%). Additionally, inositol levels in molasses may reach levels of 5,800–8,000 ppm, in which case this cofactor may be omitted as well. It is important that the pH of the solution be maintained between 5.0–7.5. This latter requirement may be addressed by analyzing the dilution water sources and adjusting extreme deviations with buffers. Approximately one quart of phosphate buffer per hundred gallons of diluted mix should meet these needs. If the parent molasses has a pH above 7, the standard addition of citric acid and phosphoric acid will adjust this to a manageable level (most molasses have a pH range of between 5–8).

Storing the material between temperatures of 60–80 degrees F is advisable to prolong the activity of ingredients. Dilutions for actual spray applications should try to achieve a final TSI between 4–10%.

The many crops to be treated may vary in requirements with respect to species, season and an assortment of environmental factors. It would then be necessary to adjust concentrations of the various ingredients. Workable alternative ranges of these concentrations along with alternative sources are presented.

In the above "Katy J" is the trademark of JKT Corporation for a mixture of polyhydroxy organic acids used as a complexing (chelating) agent. Commenting on the enhancement agents, the seaweed extract supplies plant hormones which contribute to regulation of plant metabolism; the citric acid and Katy J serve as complexing or chelating agents and assist in the transport/ingestion of other ingredients of the composition; and the xanthan gum functions as a thickening agent to solubilize ingredients that would otherwise precipitate or drop out.

The phosphate buffer was potassium phosphate.

Instead of using calcium gluconate as the source of calcium, calcium nitrate ($Ca(NO_3)_2$–4 $H_2O$) may be used as it is less expensive. Also it contributes to the nitrogen component, therefore the amount of potassium nitrate will be adjusted.

Table 1 below lists alternative concentrations of the ingredients. In a given situation a particular ingredient, normally added as such, may be present in another ingredient, e.g. in the water used to dilute the molasses or in one of the other ingredients.

As stated above certain ingredients may contain one or more other ingredients. For example, molasses will often contain some one or more of nitrogen, phosphorus, potassium and calcium, also vitamins and cofactors. Not all of such ingredients are always in the proper form. For example, some or all of the nitrogen may be in the form of proteins and some of the calcium may be in insoluble form.

TABLE 1

RANGE OF PROPORTIONS
BRIGHT SUN

| | |
|---|---|
| A. Carbon Skeleton/Energy Component | 25.00–70.00% |
| B. Macronutrient Component | |
| Nitrogen | 0.30–15.00% |
| Phosphorus | 0.20–5.00% |
| Potassium | 0.30–5.00% |
| Calcium | 0.10–5.00% |
| Magnesium | 0.05–1.50% |
| Sulfur | 0.10–5.00% |
| C. Micronutrient Component | |
| Zinc | 0.05–2.00% |
| Manganese | 0.05–2.00% |
| Iron | 0.05–2.00% |
| Copper | 0.01–0.10% |
| Boron | 0.004–0.05% |
| Molybdenum | 0.001–0.02% |
| Cobalt | 0.001–0.02% |
| D. Complexing Agent(s) | |
| Citric Acid, etc. | 0.005–5.00% |
| Lignosulfonate | 0.005–5.00–70.00% |
| E. Vitamin-Cofactor Component | |
| Folic Acid | 0.001–5.00% |
| Thiamine | 0.001–5.00% |
| Riboflavin | 0.001–5.00% |
| Nicotinic Acid | 0.001–5.00% |
| Pyridoxine | 0.001–5.00% |
| Biotin | 0.001–5.00% |
| Pantothenic Acid | 0.001–5.00% |
| Cyanocobalamin | 0.001–5.00% |
| Phosphatidylcholine | 0.001–5.00% |
| Inositol | 0.001–5.00% |
| PABA | 0.001–5.00% |
| F. Natural Source of Growth Regulator | |
| Seaweed Extract | 0.025–5.00% |
| G. Microbialstat, e.g. Proprionic Acid | 0.005–0.50% |
| H. Gum, e.g. Xanthan Gum | 0.0005–0.10 % |

Where the composition is to be sprayed, it is preferred to remove solids that will not pass through a 60 mesh screen by passing the CSE component successively through 20, 40 and 60 mesh screens and treating the concentrate or stock solution similarly for the same purpose. The pH may range is preferably 2.0 to 3.5. The stock solution (and the diluted solution ready for application) if it is stored for a substantial length of time) is preferably stored at 65° to 85° F. Dilution for end use may be to 2.5 to 12.5 percent of CSE but preferably the dilution is to 4.0 to 10.0% of CSE, percentages being by weight based on the solution.

Alternative sources of the ingredients are listed below.

Macronutrients

N—ammonium nitrate, monoammonium phosphate, ammonium phosphate sulfate, ammonium sulfate, ammonium phosphatenitrate, diammonium phosphate, ammoniated single superphosphate, ammoniated triple superphosphate, nitric phosphates, ammonium chloride, aqua ammonia, ammonia-ammonium nitrate solutions, calcium ammonium nitrate, calcium nitrate, calcium cyanamide, sodium nitrate, urea, urea-formaldehyde, urea-ammonium nitrate solution, nitrate of soda potash, potassium nitrate, amino acids, proteins, nucleic acids P—superphosphate (single, double and/or triple), phosphoric acid, ammonium phosphate, ammonium phosphate sulfate, ammonium phosphate nitrate, diammonium phosphate, ammoniated single superphosphate, ammoniated single superphosphate, ammoniated triple superphosphate, nitric phosphates, potassium pyrophosphates, sodium pyrophosphate, nucleic acid phosphates K—potassium chloride, potassium sulfate, potassium gluconate, sulfate of potash magnesia, potassium carbonate, potassium acetate, potassium citrate, potassium hydroxide, potassium manganate, potassium phosphate, potassium molybdate, potassium thiosulfate, potassium zinc sulfate Ca—calcium ammonium nitrate, calcium nitrate, calcium cyanamide, calcium acetate, calcium acetylsalicylate, calcium borate, calcium borogluconate, calcium carbonate, calcium chloride, calcium citrate, calcium ferrous citrate, calcium glycerophosphate, calcium lactate, calcium oxide, calcium pantothenate, calcium proprionate, calcium saccharate, calcium sulfate, calcium tartrate Mg—magnesium oxide, dolomite, magnesium acetate, magnesium bensoate, magnesium bisulfate, magnesium borate, magnesium chloride, magnesium citrate, magnesium nitrate, magnesium phosphate, magnesium salicylate, magnesium sulfate S—ammonium sulfate, ammonium phosphate sulfate, calcium sulfate, potassium sulfate, magnesium sulfate, sulfuric acid, cobalt sulfate, copper sulfate, ferric sulfate, ferrous sulfate, sulfur, cysteine, methionine Micronutrients Zn—zinc oxide, zinc acetate, zinc bensoate, zinc chloride, zinc citrate, zinc nitrate, zinc salicylate, ziram Fe—ferric chloride, ferric citrate, ferric fructose, ferric glycerophosphate, ferric nitrate, ferric oxide (saccharated), ferrous chloride, ferrous citrate ferrous fumarate, ferrous gluconate, ferrous succinate Mn—manganese acetate, manganese chloride, manganese nitrate, manganese phosphate Cu—cupric acetate, cupric butyrate, cupric chlorate, cupric chloride, cupric citrate, cupric gluconate, cupric glycinate, cupric nitrate, cupric salicylate, cuprous acetate, cuprous chloride B—calcium borate, potassium borohydride, borax, boron trioxide, potassium borotartrate, potassium tetraborate, sodium borate, sodium borohydride, sodium tetraborate Mo—molybdic acid, calcium molybdate, potassium molybdate, sodium molybdate Co—cobaltic acetate, cobaltous acetate, cobaltous chloride, cobaltous oxalate, cobaltous potassium sulfate, cobaltous sulfate Vitamins and Cofactors Thiamine—thiamine pyrophosphate, thiamine monophosphate, thiamine disulfide, thiamine mononitrate, thiamine phosphoric acid ester chloride, thiamine phosphoric acid ester phosphate salt, thiamine 1,5 salt, thiamine triphosphoric acid ester, thiamine triphosphoric acid salt, yeast, yeast extract Riboflavin—riboflavin acetyl phosphate, flavin adenine dinucleotide, flavin adenine mononucleotide, riboflavin phosphate, yeast, yeast extract Nicotinic acid—nicotinic acid adenine dinucleotide, nicotinic acid amide, nicotinic acid benzyl ester, nicotinic acid monoethanolamine salt, yeast, yeast extract, nicotinic acid hydrazide, nicotinic acid hydroxamate, nicotinic acid-N-(hydroxymethyl)amide, nicotinic acid methyl ester, nicotinic acid mononucleotide, nicotinic acid nitrile Pyridoxine—pyridoxal phosphate, yeast, yeast extract Folic acid—yeast, yeast extract, folinic acid Biotin—biotin sulfoxide, yeast, yeast extract, biotin 4-amidobenzoic acid, biotin amidocaproate N-hydroxysuccinimide ester, biotin 6-amidoquinoline, biotin hydrazide, biotin methyl ester, d-biotin-N-hydroxysuccinimide ester, biotin-maleimide, d-biotin p-nitrophenyl ester, biotin propranolal, 5-(N-biotinyl)-3 aminoallyl)-uridine 5'-triphosphate, biotinylated uridine 5'-triphosphate, N-e-biotinyl-lysine Pantothenic acid—yeast, yeast extract, coenzyme A Cyanocobalamin—yeast, yeast extract Phosphatidylcholine-soybean oil, eggs bovine heart, bovine brain, bovine liver, L-a-phosphatidylcholine, B-acetyl-g-O-alkyl, D-a-phosphatidylcholine(PTCn), B-acetyl-g-O-hexadecyl, DL-a-PTCh, B-acetyl-g-O-hexadecyl, L-a-PTCh, B-acetyl-g-O-(octadec-9-cis-enyl), L-a-PTCh, B-arachidonoyl, g-stearoyl, L-a-PTCh, diarachidoyl, L-a-PTCh, dibehenoyl (dibutyroyl, dicaproyl, dicapryloyl, didecanoyl, dielaidoyl, 12 diheptadecanoyl, diheptanoyl), DL-a-PTCh dilauroyl, L-a-PTCh dimyristoyl (dilauroyl, dilinoleoyl, dinonanoyl, dioleoyl, dipentadeconoyl, dipalmitoyl, distearoyl, diundecanoyl, divaleroyl, B-elaidoyl-a-palmitoyl, B-linoleoyl-a-palmitoyl) DL-a-PTCh di-O-hexadecyl (dioleoyl, dipalmitoyl, B-O-methyl-g-O-hexadecyl, B-oleoyl-g-O-hexadecyl, B-palmitoyl-g-O-hexadecyl), D-a-PTCh dipalmitoyl, L-a-PTCh, B-O-methyl-g-O-octadecyl, L-a-PTCh, B-(NBD-aminohexanoyl)-g-palmitoyl, L-a-PTCh, B-oleoyl-g-O-palmitoyl (stearoyl), L-a-PTCh, B-palmitoyl-g-oleoyl, L-a-PTCh, B-palmitoyl-a-(pyren 1-yl) hexanoyl, L-a-PTCh, B(pyren-1-yl)-decanoyl-g-palmitoyl, L-a-PTCh, B-(pyren-1-yl)-hexanoyl-g-palmitoyl, L-a-PTCh, B-stearoyl-g-oleoyl Inositol—inositol monophosphate, inositol macinate, myo-inositol, epi-inositol, myo-inositol 2,2'anhydro-2-c-hydroxymethyl (2-c-methylene-myoinositol oxide), D-myo-inositol 1,4-bisphosphate, DL-myo-inositol 1,2-cyclic monophosphate, myo-inositol dehydrogenase, myo-inositol hexanicotinate, inositol hexaphosphate, myo-inositol hexasulfate, myo-inositol 2-monophosphate, D-myo-inositol 1-monophosphate, DL-myo-inositol 1-monophosphate, D-myo-inositol triphosphate, scyllo-inositol PABA—m-aminobenzoic acid, O-aminobenzoic acid, p-aminobenzoic acid butyl ester, PABA ethyl ester, 3-ABA ethyl ester Complexing Agents Citric acid; Ca, K, Na and ammonium lignosulfonates, fulvic acid, ulmic acid, humic acid, Katy-J, EDTA, EDDA, EDDHA, HEDTA, CDTA, PTPA, NTA.

Growth Regulators

Seaweed extract—kelp extract, kinetin, kinetin riboside, benzyladenine, zeatin riboside, zeatin, extract of corn cockle, isopentenyl adenine, dihydrozeatin, indoleacetic acid, phenylacetic acid, indole ethanol, indoleacetaldehyde, indoleacetonitrile, gibberellins (e.g. GA1, GA2, GA3, GA4, GA7, GA38 etc.)

Gum Components

Xanthan gum—guar gum, gum agar, gum accroides, gum arabic, gum carrageenan, gum damar, gum elemi, gum ghatti, gum guaiac, gum karya, locust bean gum, gum mastic, gum pontianak, gum rosin, gum storax, gum tragacanth Microbialstats Proprionic acid, benzoic acid, sorbic acid.

CSE Components sugar—mannose, lactose, dextrose, arythrose, fructose, fucose, galactose, glucose, gulose, maltose, polysaccharide, raffinose, ribose, ribulose, rutinose, saccharose, stachyose, trehalose, xylose, xylulose, adonose, amylose, arabinose, fructose phosphate, fucose-p, galactose-p, glucose-p, lactose-p, maltose-p, mannose-p, ribose-p, ribulose-p, xylose-p, xylulose-p, deoxyribose, corn steep liquor, whey, corn sugar, corn syrup, maple syrup, grape sugar, grape syrup, beet sugar, sorghum molasses, cane molasses, calcium lignosulfonate sugar alcohol—adonitol, galactitol, glucitol, maltitol, mannitol, mannitol-p, ribitol, sorbitol, sorbitol-p, xylitol organic acids—glucuronic acid, a-ketoglutaric acid, galactonic acid, glucaric acid, gluconic acid, pyruvic acid, polygalacturonic acid, saccharic acid, citric acid, succinic acid, malic acid, oxaloacetic acid, aspartic acid, phosphoglyceric acid, fulvic acid, ulmic acid, humic acid nucleotides and bases—adenosine, adenosine-p, adenosine-p-glucose, uridine, uridine-p, uridine-p-glucose, thymine, thymine-p, cytosine, cytosine-p, guanosine, guanosine-p, guanosine-p-glucose, guanine, guanine-p, NADPH, NADH, FMN, FADH Buffers phosphate buffer—acetate buffer, AMP buffer, calcium tartrate, glycine buffer, phosphate citrate buffer, tris buffer Of the macronutrients listed above, the most important are N, P, K and Ca but this component preferably also includes magnesium and sulfer.

Of the micronutrients listed above, the most important are Zn, Fe and Mn, but this component preferably also includes the others in the list.

If it is desired to employ such a composition including beneficial micro-organisms, the compositions of Examples 2 and 3 may be used.

EXAMPLE 2

Soil Amendment

| Item | Concentration | Source |
|---|---|---|
| Part I Mix | | |
| Example 1 composition | As in Example 1 | |
| Katy-J Complexing Agent | 5 gr/gal mix | Katy-J (JKT Corp.) |

-continued

| Item | Concentration | Source |
|---|---|---|
| Part II Mix | | |
| *Gloeocapsa sp.* | 1 trillion cfu per gallon mix | fermentation cultures of |
| *Streptomyces griseus* | 1 trillion cfu per gallon mix | fermentation cultures of |
| *Gleocladium roseum* | 1 trillion cfu per gallon mix | fermentation cultures of |
| *Bacillus subtilis* | 1 trillion cfu per gallon mix | fermentation cultures of |
| *Pseudomonas fluorescens* | 1 trillion cfu per gallon mix | fermentation cultures of |
| Cellulase | 2,500 units/gal | Type VII from *Penicillium funiculosum* |
| Alpha amylase | 36,000 units/gal | Type XA from *Aspergillus oryzae* |
| Glycerol | 2 qt./gal | glycerol |
| Buffer | 8 oz./gal | phosphate buffer |
| Zinc sulfate | 0.05% w/v | zinc sulfate |
| Manganese sulfate | 0.05% w/v | manganese sulfate |
| Iron sulfate | 0.05% w/v | Ferrous sulfate |

The alga species, Gloeocapsa, is cultured in one-half strength Hoagland's Solution supplemented with one gram per 100 gallons mix of Katy-J. The culture suspension is aerated and provided with constant lighting (via submersible incandescent lamps with an output of light equivalent to approximately 2.0 Einsteins of light energy per square meter per hour). Approximate duration of incubation is 5–7 days. All culturing is conducted under aseptic conditions.

*Gleocladium roseum, B. subtilis, S. griseus* and *Ps. fluorescens* are cultured in fermentation tanks similar to that for Gloeocapsa but without lighting and with a different substrate. Nutrient broth (8 gr/L) is supplemented with Bright Sun (0.4% v/v). *Pseudomonas fluorescens* is a fast grower and is generally mature within 48 hours culturing time. The remaining three species require a minimum culturing period of 72 hours and in many cases 120 hours. All operations are conducted aseptically, under constant, low aeration and at 25 degrees C.

When mature, the cultures are aliquanted and blended with glycerol, phosphate buffer and enzymes. They are placed in breathe-cap containers and refrigerated immediately (5 degrees C). Application involves delivery through the irrigation system or comparable means of approximately one gallon Part I Mix+1 quart part II Mix per acre (rate may vary with soil condition).

EXAMPLE 3

Soil Treatment Tests

Use of Morning Sun[1] for soil treatment is recommended for soils which are one or more of the following: (1) alkaline, (2) high in salts, (3) high in clay; also soils which have one or more of the following properties: (4) slow infiltration rates, (5) are low in organic matter, (6) are infertile due to minerals being tied up and unavailable for assimilation, (7) are infested with disease inocula.

[1] "Morning Sun" is the name given to the composition of Example 2.

Alkaline soils are benefitted by microbial activity stimulated by Morning Sun, such activity acting to reduce pH and also to generate a mucilage which is a good soil conditioner.

Soils high in salts benefit from the increase in infiltration rate caused by Morning Sun.

With regard to clay, the texture of clay is altered by such microbial activity, becoming more granular. This in turn leads to enhanced infiltration rates. Due to such microbial activity, organic matter is also increased which benefits the soil.

Where the soil is infertile due to tying up of minerals, the complexing agent, especially lignosulfonate, solubilizes minerals and makes them available to plants.

With regard to disease inocula, Morning Sun stimulates the growth of antagonists.

Experiments were carried out Sep. 2–Nov. 10, 1989 as follows: Morning Sun was applied at the rate of 0.1 gallon on each of two 400 square foot plots and was applied with about 1100 gallons of water.

Random samples of soil from the treated plots, likewise random samples of soil from adjacent untreated plots, were examined by standard technique to determine microbial counts.

The soil was also evaluated by standard techniques for soil aggregation and for infiltration rates. Results are summarized as follows:

| Microbial Counts | |
|---|---|
| Treated | Control |
| 164 | 11.25 |

Each figure is the mean of four samples.

| Soil Aggregate Tests | |
|---|---|
| Treated | Control |
| 2 | 5 |

These are mean values of four samples each and indicate degree of cloudiness of the air dried soil swirled in water. Less cloudiness indicates more aggregation of the soil.

| Infiltration Test | |
|---|---|
| Treated | Control |
| 0.45 inch per hour | 0.15 inch per hour |

These figures indicate greater infiltration/permeability of the treated soil.

However it is preferred to use a composition as set forth in Table 2 below which does not contain added micro-organisms and to rely upon micro-organisms naturally present in the soil.

TABLE 2

| Component | % by wt of active ingredient | % by wt of component based on complete mix | Final concentration of active ingredient based on wt of complete mix |
|---|---|---|---|
| High Brix Cane or Beet Molasses | 50.0% Sugar | 32.0% | 16.0% Sugars |
| Calcium Lignosulfonate | 50.0% CaLignosulfonate | 32.0% | 16.0% CaLignosulfonate |
| Urea | 23.0% N | 5.0% | |
| $KNO_3$ | 13.9% N | 3.8% | 1.7% total Nitrogen |
| $KNO_3$ | 38.7% K | | 1.5% Potassium |
| $H_3PO_4$ | 23.7% P | 3.4 | 0.8% Phosphorus |
| $ZnSO_4$-$7H_2O$ | 36.0% Zn | 0.8% | 0.3% Zinc |

TABLE 2-continued

| Component | % by wt of active ingredient | % by wt of component based on complete mix | Final concentration of active ingredient based on wt of complete mix |
|---|---|---|---|
| $FeSO_4\text{-}7H_2O$ | 31.0% Fe | 0.8% | 0.3% Iron |
| $MnSO_4\text{—}H_2O$ | 28.0% Mn | 0.8% | 0.2% Manganese |
| Vitamin B Complex | — | 1.0% | 0.04% B-Cplx |
| Water (Tap) | — | 20.4% | |

The calcium lignosulfonate was a product of Georgia-Pacific Corporation known as LIGNOSITE 50 which is described in literature of that company as a 50% aqueous solution of high purity derived from soft wood and as having the following specification.

CHEMICAL DESCRIPTION

| | |
|---|---|
| Total solids, % | 50.0 |
| Calcium lignin sulfonate, % | 40.0 |
| Methoxyl, % | 4.2 |
| Reducing sugars (as glucose), % | 3.6 |
| Calcium (soluble), % | 2.5 |
| Sodium, % | 0.5 |
| Insolubles ($CaSO_4\ 2H_2O$), % | 1.5–2.0 |
| pH of 10% solution | 5.5 |

PHYSICAL PROPERTIES

| | |
|---|---|
| Specific gravity (liquid, 25°/15° | 1.252 |
| Gallon weight, lbs | 10.4 |
| Heat of combustion, BTU/lb solids | 8100 |
| Viscosity, cp at 25° C. | 700 |

These materials are mixed as follows: The water is placed in a mixing vessel equipped with a stirrer. While stirring the calcium lignosulfonate, urea, iron sulfate, manganese sulfate, zinc sulfate, potassium nitrate and vitamin B complex are added in that order and stirring is continued until the ingredients are dissolved in the water. Then the molasses is added followed by the phosphoric acid and stirring is continued until they are dissolved. Phosphoric acid is added as needed to bring the pH to 2.5.

Alternative concentrations are provided in Table 3 below:

TABLE 3

| Component | % w/w of Mix | | Final active ingredient Conc. w/w % |
|---|---|---|---|
| High Brix Cane or Beet Molasses | 10–60% | | 5–30% |
| Ca Lignosulfonate | 10–60% | | 5–30% |
| Urea | 2–20% | | |
| | | Nitrogen | 2–20% |
| $KNO_3$ | 1–10% | | |
| $KNO_3$ | 1–10% | K | 0.5–5.0% |
| $H_3PO_4$ | 1–10% | | 0.3–3.0% |
| $ZnSO_4\text{-}7H_2O$ | 0.4–10% | | 0.1–3.5% |
| $FeSO_4\text{-}7H_2O$ | 0.4–10% | | 0.1–3.5% |
| $MnSO_4\text{—}H_2O$ | 0.4–10% | | 0.1–3.5% |
| Vit-B Complex | 0.5–10% | | 0.2–0.4% |
| Water | 15–73.3% | | |

The following examples will serve to illustrate the practice and advantages of the invention:

EXAMPLE 4

Pistachio Herbicide Strip

Orchard rows of pistachio trees were stripped with Surflan (3 quarts/acre) and Goal (6 pints/acre) in January and watered in by micro-sprinklers. Following are specifications on each herbicide:

Surflan (Elanco Chemical Company)

Oryzalin (3,5-dinitro-$N^4$, $N^4$ dipropylsulfanilide) 40.4% active ingredient.

Goal (Rohm & Haas Chemical Company)

Oxyfluorfen2-chloro-1-(3-ethoxy-4-nitrophenoxy) 4-(trifluoromethyl) benzene 19.4% active ingredient.

Each herbicide had curtailed weed growth, the treated strips being completely free of weeds. The composition of Table 1 was injected into micro-sprinkler lines at the rate of 20 gallons of such composition per acre in April. The orchard was irrigated as usual based on a demand of 4–5 acre feet per season. Weed growth was determined at the end of four weeks from treatment date and was used as a criterion and/or indicator of herbicide degradation. Microbial colony counts were taken at the end of two weeks from the date of treatment. Standard procedures were used with serial dilution to $10^{-5}$, plating 1 ml aliquots atop nutrient agar. Plates were sealed in parafilm (following air drying for eight hours) and incubated in the dark for 72 hours at 25° C.

Results

| | Replications | | | | |
|---|---|---|---|---|---|
| Treatment | 1 | 2 | 3 | 4 | Mean |
| Control | 2 | 0 | 3 | 0 | 1.2 |
| Treated | 163 | 203 | 197 | 257 | 205.0 |

Note:
Numbers represent total number of weeds in each 50 foot of strip per replicated block.

Weed species detected were pigweed, purslane, shepherd'ms purse, filavee, barnyard grass.

Microbial Population Increases.

| | Replications | | | | |
|---|---|---|---|---|---|
| Treatment | 1 | 2 | 3 | 4 | Mean |
| Control | 6 | 11 | 21 | 9 | 11.7 |
| Treated | 71 | 102 | 83 | 101 | 89.2 |

Note:
Numbers represent microbial colony counts at 72 hours following incubation; dilution = $10^{-4}$.

The proliferation of microbes in the plots treated with the Table 1 composition indicate the efficacy of the composition in breaking down the herbicides; likewise the growth of weeds.

EXAMPLE 5

Melon Study

Method

A melon field had been treated with Treflan. The melon plants were young seedlings. There was visible damage from Treflan residue, the roots of seedlings typically bent near the soil line and swollen for 3"–6" down towards the tap root. Secondly, nematode galls from diagnosed populations of *Meloidogyne incognita* (Root - Knot Nematode) were numerous overaging 16 galls per seedling (number of plants examined=20). The composition of Table 2 was shanked in at 30 gallons/acre with spades on each side of the seedling (approximately 8" on either side) at a depth of 3". Seedlings were irrigated via sprinklers to distribute the material into the root zone. One month following treatment plants were examined for top and root growth (shoot length and root girth), galling and/or stunting and root swelling and bending. Root growth was evaluated on a 0–5 scale (5=excellent).

Results were as follows:

1. Top Growth

|  | Replications | | | | | |
| --- | --- | --- | --- | --- | --- | --- |
| Treatment | 1 | 2 | 3 | 4 | 5 | Mean |
| Control | 13" | 15" | 17" | 14" | 15" | 15 |
| Treated | 38" | 27" | 39" | 43" | 45" | 38 |

Note:
Numbers represent length of longest vine per randomly selected plant.

2. Nematode Galling

|  | Replications | | | | |
| --- | --- | --- | --- | --- | --- |
| Treatment | 1 | 2 | 3 | 4 | Mean |
| Control | 25 | 32 | 27 | 41 | 32 |
| Treated | 18 | 13 | 15 | 19 | 16 |

Note:
Numbers represent galls per root (from nematode damage).

3. Root Evaluation

|  | Replications | | | | | |
| --- | --- | --- | --- | --- | --- | --- |
| Treatment | 1 | 2 | 3 | 4 | 5 | Mean |
| Control | 2 | 1 | 2 | 1 | 1 | 1.4 |
| Treated | 4 | 5 | 5 | 4 | 5 | 4.6 |

Note:
Numbers represent root evaluation ratings with a 0–5 scale and 5 = excellent status.

Treflan, a product of Elanco Chemical Company, is Trifluralin (α, α, α-trifluro-2,6-dinitro-N,N-dipropyl-p-toluidine) 44.5% active ingredient applied at 2 pints/acre.

EXAMPLE 6

Potato Study

Method

A potato field was examined with visible Assert (American Cyanamid) herbicide toxicity. Additionally, the field had also been treated with Sencor (Mobay Chemicals) herbicide. Potato vines were stunted, thin-leaved and chlorotic. The composition of Table 2 was applied at the rate of 150 gallons/acre by water through a stationary pivot which delivered a ⅛ mile strip of approximately 15' in width. Ten randomly spaced soil cone samples were taken from the area prior to treatment and sent to a laboratory for gas chromatograph analysis of Assert and Sencor. Sampling was continued at two week intervals. Additional parameters examined included:

1. full mineral analysis
2. salts, cation exchange capacity
3. total microbial population counts
4. weed growth
5. soil softness or workability The results of laboratory tests were not available at the time of filing this application. However, beneficial effects of the composition of Table 2 were quite evident. Thus stubble alongside the treated strip had not decayed indicating that micro-organisms had not proliferated which would have caused decay of the stubble whereas stubble in the treated strip had decayed. This was confirmed by micro-organism counts, such being greater in the treated strip. It is believed that laboratory tests will establish the breakdown of herbicides in the treated strip. Also noted was recovery of potato plants in the treated strip whereas there was no such recovery in the untreated soil.

Assert is a product of American Cyanamid containing 27% active ingredients which are (1) m-toluic acid, 6-(4-isopropyl-4-methyl-5-oxo-2 imidazolin-2-yl) ethyl ester and (2) p-toluic acid, 2-(4-isopropyl-4-methyl-5-oxo-2 imidazolin-2-yl) methyl ester.

Sencor is a product of Mobay Chemicals containing 41% active ingredient which is 4-amino-6-(1,1 dimethylethyl)-3-(methylthio)-1,2,4-triazine-5(4H)-one.

The vulnerability or resistance of toxic chemicals to attack and degradation by micro-organisms is influenced by several factors including the following:

1. Moisture content and oxygen level in the soil. Lack of moisture and/or oxygen favor resistance to degradation.
2. Presence of microbialstatic toxins in the soil, which may be the toxic chemical of interest or it may be another substance.
3. Temperature. Extremes of temperature, that is to say excessive cold or heat, favor resistance. Alternatively, moderate temperature favors the growth of micro-organisms which are desired.
4. Chemical interactions which immobilize substrates. For example iron or phosphorus may act to harden soil and make it impervious to the nutrient material.
5. Minimal or no access of microbes to the toxic chemical.
6. Low substrate or nutrient levels.

Commenting on the factors listed above, if there are no temperature extremes and if moisture and oxygen are abundant, i.e. factors 1 and 3 are favorable, if an abundant nutrient (substrate) level is available, factors 2, 4 and 5 can be overcome. Thus favorable factors 1 and 3 combined with favorable factor 6 will cause microbial communities to increase dramatically and this will mitigate unfavorable factors 2, 4 and 5. As the microbial population increases the chemical degrading and detoxifying effects will increase. For example if a chemical, or a partial degradation product of a chemical, is resistant to a particular species of micro-organism, an increase in the population of that species may overcome the difficulty (a mass effect) or a mutated species may evolve which is effective. The multiplication of many species is favorable because the chance of an effective species (effective to degrade a chemical) being multiplied is enhanced by favorable factors 1, 3 and 6.

Commenting further on the description above of the invention:

The preferred composition of Table 2 is simpler than the composition of Example 1 which is a preferred composition for use as a foliar spray. The Example 1 composition may be used for purposes of the present invention but certain of the minerals are naturally present in soil, hence need not be included in the composition of Table 2 intended for soil treatment. For example magnasium, boron, cobalt, molybdenum and copper are omitted because they are normally present in soil. Also, in the mixing procedure of Example 1 molasses is added first whereas in the mixing procedure for Table 2 it is added next to last. I have found that the presence (as is normal) of dissolved solids in molasses in relatively high proportion inhibits dissolving of other minerals. Calcium lignosulfonate is advantageous in the present invention because it is not colonized, therefore is not consumed as rapidly by micro-organisms as is molasses and other sugar sources. The approximately equal proportions of calcium lignosulfonate and molasses in the composition of Table 2 provide a longer lasting substrate for micro-organisms; i.e. after most or all of the molasses has been consumed there is still calcium lignosulfonate to provide a substrate. Further, the initial breakdown products of calcium lignosulfonate are humic acids which are good substrates and good complexing agents.

Discussion of Components (1) The Assimilable carbon Skeleton/Energy (CSE) Component The function of this component is to supply carbon skeleton for synthesis of proteins and other molecules and to supply energy for metabolism. Water soluble carbohydrates such as sucrose, fructose, glucose and other di- and monosaccharides are suitable, most commonly in the form of molasses or other byproducts of food manufacture. Commercially available lignosulfonates, discussed below under the heading "Complexing Agents," are also suitable as a CSE source inasmuch as they commonly contain sugars. It is not preferred to use lignosulfonate as a complete substitute for molasses, soluble starch or other carbohydrate in a foliar spray because it has a toxic effect when employed in large amount but for purposes of soil treatment it may be used as a complete substitute for molasses or other soluble carbohydrate and is preferably used in relatively large proportions, e.g. ½ molasses and ½ lignosulfonate.

(2) The Macronutrient Component

The macronutrients are essential to nutrition and growth. Where some of them are present in adequate quantity in the soil, they may be omitted.

The most important macronutrients are N, P and K.

(3) Micronutrient Component

The most important micronutrients are Zn, Fe and Mn. The others may be omitted but their presence is preferred unless they are present in the soil.

(4) Vitamin/Cofactor Component

The most important are folic acid, biotin, pantothenic acid, nicotinic acid, riboflavin and thiamine. Others may be omitted but their presence is preferred.

(5) Complexing Agents

The function of this component, aside from its use as a CSE agent, is to solubilize other components of the composition which otherwise may precipitate and become non-assimilable or difficultly assimilable and to mobilize minerals in the soil which might otherwise be unavailable to micro-organisms.

A complexing agent such as citric acid, humic acids, lignosulfonate, etc. serves to tie up ions such as iron and other ions and prevent them from forming precipitates. In some cases, e.g. with EDTA, this complexing is by way of a process of chelation. The macronutrient or micronutrient so complexed nevertheless remains assimilable.

It will therefore be apparent that new and useful compositions for and methods of detoxification of soil have been provided.

I claim:

1. A method for treating soil and to effect an increase in microbiota population in the soil, the method comprising contacting the soil with a composition comprising:

from about 2.5 to about 12.5 weight percent of molasses;

from about 0.5 to about 12.5 weight percent of a complexing agent selected from the group consisting of calcium lignosulfonate, potassium lignosulfonate, sodium lignosulfonate, ammonium lignosulfonate and mixtures thereof;

a nitrogen nutrient source in an amount effective to provide from about 0.03 to about 2.7 weight percent nitrogen in the form of ammonia or urea or mixtures thereof; and a phosphorus nutrient source in an amount effective to provide from about 0.02 to about 0.90 weight percent phosphoric acid.

2. A method for treating soil to effect an increase in microbiota population in the soil, the method comprising contacting the soil with an aqueous composition comprising:

from about 2.5 to about 12.5 weight percent water soluble carbon skeleton/energy component, the carbon skeleton/energy component selected from the group consisting of mannose, lactose, dextrose, arythrose, fructose, fucose, galactose, glucose, gulose, maltose, polysaccharide, raffinose, ribose, ribulose, rutinose, saccharose, stachyose, trehalose, xylose, xylulose, adonose, amylose, arabinose, fructose phosphate, fucose-p, galactose-p, glucose-p, lactose-p, maltose-p, mannose-p, ribose-p, ribulose-p, xylose-p, xylulose-p, deoxyribose, adonitol, galactitol, maltitol, mannitol, mannitol-p, ribitol, sorbitol, sorbitol-p, xylitol and mixtures thereof;

from about 0.5 to about 12.5 weight percent of a complexing agent selected from the group consisting of calcium lignosulfonate, potassium lignosulfonate, sodium lignosulfonate, ammonium lignosulfonate and mixtures thereof;

a nitrogen nutrient source in an amount effective to provide from about 0.03 to about 2.7 weight percent nitrogen in the composition, the nitrogen nutrient source being selected from the group consisting of ammonia, urea, ammonium salts, nitrates, amino acids, proteins, nucleic acids and mixtures thereof; and a phosphorus nutrient source in an amount effective to provide from about 0.02 to about 0.90 weight percent phosphorus in the composition, the phosphorus nutrient source being selected from the group consisting of phosphoric acid, single, double and triple super phosphates, salts of phosphoric acid, nitric phosphates, pyrophosphates, nucleic acid phosphates, and mixtures thereof.

3. A method in accordance with claim 2 wherein the water soluble carbon skeleton/energy component is molasses.

4. A method in accordance with claim 3 wherein the phosphorus nutrient source comprises phosphoric acid.

5. A method in accordance with claim 4 wherein the nitrogen nutrient source comprises urea or aqua ammonia.

6. The method of claim 2 or claim 1 in which the soil is so treated without the addition of microbiota from a source external to the soil.

7. A method of degrading a toxic organic chemical in soil, such chemical or a precursor thereof having been added to the soil or to plants grown in the soil as a herbicide or pesticide, such method comprising:

(a) mixing with the soil a nutrient in quantity and under such conditions that it causes rapid proliferation of microorganisms added to or naturally present in the soil which directly attack and degrade such organic chemical or which acquire the ability to do so;

(b) such mixing being under conditions which cause rapid proliferation of the microorganisms and of microorganisms which are capable of using the chemical as a nutrient and (c) allowing such proliferation to continue until the added nutrient is depleted and the microorganisms attack and degrade the chemical as a nutrient source, wherein the nutrient comprises:

from about 2.5 to about 12.5 weight percent water soluble carbon skeleton/energy component, the carbon skeleton/energy component selected from the group consisting of mannose, lactose, dextrose, arythrose, fructose, fucose, galactose, glucose, gulose, maltose, polysaccharide, raffinose, ribose, ribulose, rutinose, saccharose, stachyose, trehalose, xylose, xylulose, adonose, amylose, arabinose, fructose phosphate, fucose-p, galactose-p, glucose-p, lactose-p, maltose-p, mannose-p, ribose-p, ribulose-p, xylose-p, xylulose-p, deoxyribose, adonitol, galactitol, maltitol, mannitol, mannitol-p, ribitol, sorbitol, sorbitol-p, xylitol and mixtures thereof;

from about 0.5 to about 12.5 weight percent of a complexing agent selected from the group consisting of calcium lignosulfonate, potassium lignosulfonate, sodium lignosulfonate, ammonium lignosulfonate and mixtures thereof;

a nitrogen nutrient source in an amount effect to provide from about 0.03 to about 2.7 weight percent nitrogen in the composition, the nitrogen nutrient source selected from the group consisting of ammonia, urea, ammonia salts, nitrates, amino acids, proteins, nucleic acids and mixtures thereof; and a phosphorus nutrient source in an amount effective to provide from about 0.02 to about 0.9 weight percent phosphorus, the phosphorous nutrient source being selected from the group consisting of phosphoric acid, single, double and triple super phosphates, salt of phosphoric acid, nitric phosphates, pyrophosphates, nucleic acid phosphates, and mixtures thereof.

8. The method of claim 7 wherein the micro-organisms are primarily or entirely those present in the soil before incorporating the nutrient medium.

9. The method of claim 7 in which the nutrient further includes a vitamin/co-factor component selected from the group consisting of thiamine, riboflavin, nicotinic acid, pyridoxine, folic acid, biotin, pantothenic acid, cyanocobalamin, phosphatidylcholine, inositol, para-aminobenzoic acid, and mixtures thereof.

10. The method of claim 9 wherein the vitamin/co-factor component is selected from the group consisting of folic acid, riboflavin, thiamine and mixtures thereof.

11. The method of claim 7 in which the lignosulfonate acts as a complexing agent and also as a carbon skeleton/energy component and is present in a quantity sufficient to contribute substantially to the carbon skeleton/energy requirements of said micro-organisms.

12. The method of claim 7 wherein the carbon skeleton/energy component is molasses.

13. The method of claim 7 or claim 12 wherein the phosphorus nutrient source comprises phosphoric acid and the nitrogen nutrient source comprises urea or aqua ammonia.

* * * * *